United States Patent [19]

Kleinhammer et al.

[11] Patent Number: 4,467,030

[45] Date of Patent: Aug. 21, 1984

[54] DETERMINATION OF THE THYROXINE-BINDING INDEX IN SERUM

[75] Inventors: Gerd Kleinhammer, Tutzing; Gerlinde Deutsch, Pöcking; Hans-Ralf Linke, Raisting; Fritz Stähler, Tutzing; Wolfgang Gruber, Tutzing-Unterzeismering, all of Fed. Rep. of Germany

[73] Assignee: Boehringer Mannheim GmbH, Mannheim, Fed. Rep. of Germany

[21] Appl. No.: 263,948

[22] Filed: May 15, 1981

Related U.S. Application Data

[63] Continuation of Ser. No. 045,373, Jun. 4, 1979, abandoned.

[30] Foreign Application Priority Data

Jun. 12, 1978 [DE] Fed. Rep. of Germany ....... 2825650

[51] Int. Cl.$^3$ ............... G01N 33/54; G01N 33/58; G01N 33/78
[52] U.S. Cl. ..................... 435/7; 435/810; 436/500; 436/527; 436/810
[58] Field of Search ............ 435/7, 188, 177, 810; 436/500

[56] References Cited

U.S. PATENT DOCUMENTS

| | | | |
|---|---|---|---|
| 3,850,752 | 11/1974 | Schuurs et al. | 435/188 |
| 3,962,039 | 6/1976 | Bates | 435/7 |
| 4,040,907 | 8/1977 | Ullman et al. | 435/188 |
| 4,043,872 | 8/1977 | Blakemore et al. | 435/7 |
| 4,052,504 | 10/1977 | Hertl et al. | 436/500 |
| 4,158,703 | 6/1979 | Polito | 436/500 |
| 4,168,207 | 9/1979 | Yoshida et al. | 435/7 |

OTHER PUBLICATIONS

Schall, et al., "A Sensitive Manual Enzyme Immuno Assay for Thyroxine", *Clin. Chem.*, vol. 24, No. 10, (1978), pp. 1801–1804.

Kleinhammer, et al., "Enzyme Immuno Assay for Determination of Serum Thyroxine in Antibody Coated Tubes", *Clin. Chem.*, vol. 23, No. 6, (1977), p. 1123.

Kleinhammer et al., "Enzyme Immunological Determination of T$_4$ and T$_3$ in Antibody-Coated Glass Tubes", *Chem. Absts.*, vol. 89, No. 7, p. 260, (1978), Abs. No. 55950c.

*Primary Examiner*—Sidney Marantz
*Attorney, Agent, or Firm*—Felfe & Lynch

[57] ABSTRACT

A method for the determination of the thyroxine-binding index in serum, which method comprises mixing the serum sample to be determined with a defined amount of thyroxine and a defined amount of a determinable enzyme covalently bound to thyroxine, contacting the resulting solution with anti-thyroxine antibodies present in the solid phase, separating the liquid phase from the solid phase, and measuring the activity of said determinable enzyme in one of the phases as a measure of the tyroxine-binding index in said serum sample.

8 Claims, No Drawings

DETERMINATION OF THE THYROXINE-BINDING INDEX IN SERUM

This is a continuation of application Ser. No. 045,373, filed June 4, 1979, abandoned.

The present invention is concerned with a method and a reagent for the determination of the thyroxine-binding index in serum.

Because of the wide extent of thyroid gland investigations, thyroid gland diagnosis is of special importance in clinical chemistry. The basic in vitro thyroid gland diagnosis includes the determination of the total thyroxine present in the serum (total $T_4$), as well as the determination of the concentration of the thyroxine-binding globulin (TBG), which takes place with the help of the so-called triiodothyronine uptake ($T_3$ uptake) or thyroxine-binding index (TBI test).

The above-mentioned $T_3$ uptake test is used to determine the residual binding capacity (RBK) of carrier proteins for thyroid gland hormones in the serum. These proteins are thyroxine-binding globulin (TBG), to which is bound about 60% of the total $T_4$ amount present, as well as thyroxine-binding prealbumin (TBPA) and albumin. Consequently, this residual binding capacity is substantially a question of the binding of the thyroid gland hormones on to the TBG. Thus, in the case of hyperthyreosis with, for example, an increased $T_4$ content, more binding sites of the carrier protein are occupied by the thyroid gland hormones $T_4$ and $T_3$, whereas, in the case of hypothyreosis, less binding sites of the carrier protein are occupied by the thyroid gland hormones $T_4$ and $T_3$.

In the case of a known process for the determination of the TBI, a definite amount of radioactive $T_3$ is mixed with a serum sample and an anion exchanger. The free binding sites of the carrier protein and of the anion exchanger compete for the radioactive $T_3$. The more unoccupied binding sites are present on the carrier protein, then the more radioactive $T_3$ is bound thereon, the remainder going on to the ion exchanger. Evaluation is carried out by measuring the radioactivity either on the ion exchanger or in the solution. The ratio of the radioactivity in the solution, which corresponds to that amount of radioactive $T_3$ which is bound on to the carrier proteins of the serum to be investigated, to the radioactivity in the solution of a standard sample, multiplied with a specific factor for the standard gives the so-called thyroxine-binding index TBI.

A disadvantage of this known process is the necessity of having to use radioactive substances. This requires, on the one hand, expensive and complicated measurement devices and, on the other hand, the handling of radioactive reagents, which is made difficult due to the legal requirements because of the potential damage to health of these substances.

Therefore, it is an object of the present invention to provide a process for the TBI determination which does not suffer from these disadvantages and enables, with the use of simple measuring devices present in every laboratory, a dependable determination of the TBI index for thyroid gland diagnosis to be carried out.

Thus, according to the present invention, there is provided a process for the determination of the thyroxine-binding index in serum, wherein a serum sample to be investigated is mixed with a definite amount of thyroxine and a definite amount of a determinable enzyme covalently bound to thyroxine, the solution obtained is contacted with antithyroxine antibodies present in the solid phase, the liquid phase is separated from the solid phase and the activity of the determinable enzyme employed is measured on one of the phases.

The present invention is based upon the consideration that replacement of the radioactive marking in the known $T_3$ uptake test by an enzyme marking, with the use of an easily determinable enzyme as marker, could solve the problem. However, experiments which have been carried out showed that it is not possible, in the case of the known $T_3$ uptake test, to replace radioactively marked $T_3$ ($T_3$-$I_{125}$) by enzyme-marked $T_3$ or $T_4$, which would be preferable. Thus, it transpired that enzyme-marked $T_3$ or $T_4$ is not bound by the sites on the serum proteins capable of binding. It is assumed that this is due to the voluminous enzyme residue which sterically hinders binding.

Surprisingly, however, we have found that enzyme-marked $T_4$ is able to compete with non-enzyme-marked $T_4$ for anti-$T_4$ antibodies which are present in the solid phase. Therefore, in the process according to the present invention, on the one hand, the bindable places of the serum protein and those of the insoluble anti-$T_4$ antibodies compete for the $T_4$, whereby the more $T_4$ is bound on to the anti-$T_4$ antibodies, the less free binding sites are present in the serum. At the same time, enzyme-marked $T_4$ competes with non-marked $T_4$ for the anti-$T_4$ antibodies. Therefore, the more enzyme-marked $T_4$ is bound on to the solid phase, the greater is the thyroxine-binding capacity of the serum and thus the thyroxine-binding index TBI. Therefore, the measured enzyme activity in the solid phase represents a direct measure for the magnitude of the TBI. However, the activity can also be determined in the liquid phase.

According to the present invention, use can be made of any determinable enzyme which, without loss of its enzymatic activity, can be bound to thyroxine, those marking enzymes being preferably used, the activity of which can easily be determined by an optical test and especially by a color reaction in visible light or by change of the NADH concentration. Typical examples of marking enzymes which can be used include peroxidase, glucose oxidase, α- and β-glactosidase, glucoamylase, invertase and alkaline phosphatase.

For all the above-mentioned enzymes, simple and rapid determination methods are known, with regard to which reference is made, for example, to H. U. Bergmeyer's "Methoden der enzymatischen Analyse", pub. Verlag Chemie, 3rd edition, 1974. The anti-$T_4$ antibody present in the solid phase can be free of a carrier, for example rendered insoluble by cross-linking with a polyfunctional reagent, such as a dialdehyde, dioxide or the like. However, the antibody is preferably bound to a solid carrier material. The solid carrier for the anti-$T_4$ antibody can be any material which is inert towards the substances employed in the test on to which the mentioned antibody can be bound. We have found that, in the case of numerous materials, the anti-$T_4$ antibody can be sufficiently securely bound by adsorptive forces to the surface of the carrier material. However, if desired, the antibody can also be fixed by methods conventionally used for fixing biologically-active proteins on to solid carrier materials, for example via covalent bonds. Typical examples of this include the activation of the carrier surface by the cyanogen bromide method, by protein copolymerisation and by surface cross-linking of the antibody on to the carrier by means of polyfunctional cross-linking agents, such as glutardialdehyde or the like, these methods being well known.

According to the present invention, it is preferable to use containers, such as test tubes, the inner wall of which is coated with the antibody. Typical examples of container materials which can be used include polystyrene and styrene-acrylonitrile copolymers, as well as other synthetic resins and glass. In the case of synthetic resins based on styrene, a sufficient coating can be obtained merely by leaving an antibody solution in the container for some time.

The above remarks apply analogously to carrier materials which are not in the form of containers but are, for example, in the form of particles which can be used for column packings.

Anti-$T_4$ antibodies are prepared by the usual methods for obtaining antibodies against hormones, the use of a conjugate of $T_4$ on to an appropriate carrier protein being preferred as immunogen. Of the large number of well-known carrier proteins, bovine serum albumin (BSA) is especially preferred. The carrier proteins are coupled chemically with the $T_4$, for example with glutardialdehyde in a weakly alkaline medium, followed by reduction with sodium borohydride. Another coupling method which can be used is the reaction with morpholino-dicyclohexyl-carbodiimide. Experimental animals for the administration of the so obtained $T_4$ immunogen include, for example, rabbits or sheep but other animals can also be used.

The preparation of $T_4$ marked with peroxidase, which is preferred according to the present invention, can be carried out by the reaction of tert.-butyloxy-carbonyl-thyroxine-N-hydroxysuccinimide with peroxidase (POD), followed by chromatographic purification of the product obtained. Most other enzymes coming into consideration can also be bound in the same manner, as well as with the use of other known protein-chemical processes.

As mentioned above, according to the present invention, a definite amount of $T_4$ is used. We have found that this amount is preferably from 100 to 500 ng.$T_4$/ml. of serum, although greater or smaller amounts can also be used. However, the above-mentioned range of amounts covers practically all serum compositions which occur and, consequently, suffices for hyperthyroid as well as for hypothyroid sera. The amount of enzyme-marked $T_4$ added depends upon the nature of the particular enzyme employed and especially upon the specific activity of this enzyme which can still be easily determined. In the case of the preferred marking with POD, such an amount is preferably added that the actual test mixture contains from about 1 to about 200 mU POD/ml.

The reaction mixture of serum, buffer, $T_4$ and enzyme-marked $T_4$ is contacted with insoluble and preferably carrier-bound anti-$T_4$ antibody for a time which is sufficiently long to give a constant binding rate of the marked $T_4$ on to the antibody. The period of time depends, to a certain extent, upon the conditions with regard to pH value, temperature and concentration. In general, a period from about 30 minutes to about 2 hours is sufficient. When incubation is completed, the solution is separated from the carrier, for example by pouring out of the container used, the carrier is washed with water and subsequently the determination of the carrier-bound enzyme activity is carried out. In the case of the preferred embodiment using a container carrier and using POD as the marking enzyme, there is added, for example, hydrogen peroxide and ABTS (Trademark for [2,2'-azino-di-(3-ethylbenzthiazoline-6-sulphonate)]) in a buffer solution, the extinction difference being determined at a measurement wavelength of 405 nm.

The present invention also provides a test kit for carrying out the process according to the present invention, which test kit consists essentially of thyroxine, enzyme-marked thyroxine, anti-thyroxine antibody in the form of insoluble solid material, a buffer and a reagent for the determination of the enzyme activity. Buffers which can be used are those with which a pH value of from 7.5 to about 9.3 can be adjusted, a pH value of from 8.0 to 9.0 being preferred. Typical examples of buffers which can be used in the given range include phosphate buffer, tris buffer, borax buffer and barbital buffer, 0.05 to 0.5M barbital buffer being preferred.

The test kit according to the present invention can also contain conventional stabilizing agents, such as bovine serum albumin, carbohydrates and/or glycerol, as well as immune reaction-promoting additives.

As enzyme-marked $T_4$, the test kit according to the present invention preferably contains thyroxine-peroxidase. The reagent for the determination of the enzyme activity can then, in this preferred case, comprise hydrogen peroxide or a compound which provides hydrogen peroxide, such as sodium perborate or perhydrite, as well as 2,2'-azino-di-(3-ethylbenzthiazoline-6-sulphonate), usually referred to as ABTS, and also an appropriate buffer. A typical example of an appropriate buffer is phosphate-citrate buffer (pH 4.5 to 6.0). Another reagent which can be used for this embodiment comprises phosphate buffer (pH 7.0), guaiacol and hydrogen peroxide.

A special embodiment of the preferred test kit of the present invention comprises or contains:

| | |
|---|---|
| thyroxine | 100–440 ng./ml. |
| thyroxine-POD | 5–100 mU/ml. |
| barbital buffer (pH 8.6) | 0.1–0.2 M |
| bovine serum albumin | 0.2% |
| anti-thyroxine antibody (calculated without carrier) | 1–0.05 µg /ml. |
| hydrogen peroxide | 0.5–5 mM/l. |
| ABTS | 5–50 mM/l. |
| phosphate-citrate buffer (pH 5.0) | 0.1–0.2 M |

For the preparation of the enzyme-marked thyroxine, it is preferable to start from tert.-butyloxycarbonyl-thyroxine-N-hydroxysuccinimide, the reaction taking place in buffer/dimethylformamide solution (1:1 v/v). The buffer used is that which is best suited for the particular enzyme used. Phenylbutylamine-sepharose has proved to be useful for the purification of the conjugate.

Thus, the present invention provides a simple process, which can be carried out with conventional laboratory devices, for the determination of the thyroxine-binding index of serum, the exactitude of which corresponds to that of the known methods using radioactive marking but does not suffer from their disadvantages.

The following Example is given for the purpose of illustrating the present invention:

EXAMPLE

A. Preparation of anti-thyroxine antibodies.

Thyroxine is coupled to bovine serum albumin in aqueous solution (pH 10) by the addition of 1.9% by weight glutardialdehyde. The Schiff base bond is then reduced with excess sodium borohydride and the T4 immunogen obtained is purified by chromatography. The product obtained is dialyzed and then administered to the experimental animals.

B. Preparation of T4-POD

POD is reacted with a 10 fold molar excess of tert.-butyloxycarbonylthyroxine-N-hydroxysuccinimide in dimethylformamide/phosphate buffer (pH 8.5) (1:1 v/v). The dimethylformamide is then dialyzed off and the aqueous solution is passed over phenylbutylamine-sepharose. The column is washed with tris-sodium chloride buffer and then with 1M sodium chloride-containing ethylene glycol/water mixture (1:1 v/v). The eluate is stirred for 2 hours with 0.5M hydroxylamine and subsequently dialyzed against phosphate buffer. The solution obtained is mixed with bovine serum albumin and lyophilised.

C. Preparation of carrier-bound anti-T4 antibodies.

Anti-T4 antiserum is obtained in known manner from the immunised experimental animals and precipitated with ammonium sulphate. The precipitate is taken up with 0.04M phosphate buffer 1:6000. 1.5 ml. of the solution so obtained is left to stand overnight in test tubes made of styrene-acrylonitrile polymer (available under the Trademark "Luran"), then sucked out and washed with physiological sodium chloride solution which contains 1% BSA and thereafter dried.

D. Carrying out the determination.

Into the anti-T4 antibody-coated test tubes obtained according to C above are pipetted 10 μl. serum and subsequently 1 ml. of a reagent which contains 280 ng T4/ml., 10 mU/ml. T4-POD in 0.12M barbital buffer (pH 8.6) and 0.2% bovine serum albumin. After standing for 2 hours at ambient temperature, the test tubes are emptied by sucking out and the POD reagent is placed therein, the latter comprising 1.47 mM/l. hydrogen peroxide and 14 mM/l. ABTS in 0.2M phosphate-citrate buffer (pH 5.0). The color change which occurs is measured at 405 nm.

For the evaluation, a calibration line is produced with 2 standards of differing T4-binding capacity which are treated in the same way as the samples, the reciprocal values of the extinctions measured for these standards being plotted either against the T4 amounts bound by the standards or directly against the previously determined TBI values of these standards.

E. Use of the method for the investigation of human sera.

83 Human sera samples are comparatively investigated by the process according to the present invention and with the use of a commercially available method using $T_3-I_{125}$. If the investigated sera are classified on the basis of the particular TBI values obtained with reference to the normal range valid for the method in question in those sera with reduced, normal and increased T4-binding capacity, then a satisfactory agreement results between both methods (see Table 1).

TABLE 1

Comparison of the process according to the present invention for the determination of the TBI (A) with a conventional TBI radio-assay (B), using human serum samples (n = 83)

| A | B | | |
|---|---|---|---|
|   | 1 | 2 | 3 |
| 1 | 28 | 1 |   |
| 2 | 1 | 28 |   |
| 3 |   | 3 | 22 |

1 reduced  
2 normal    } T4-binding capacity  
3 increased

It will be understood that the specification and examples are illustrative, but not limitative of the present invention and that other embodiments within the spirit and scope of the invention will suggest themselves to those skilled in the art.

What is claimed is:

1. Method for determining the thyroxine-binding index in serum comprising:
   (a) mixing a sample of the serum with (1) a predetermined amount of thyroxine and (2) a predetermined amount of enzyme-labeled thyroxine;
   (b) contacting the solution resulting from step (a) with insolubilized anti-thyroxine;
   (c) separating the resulting liquid phase from the resulting solid phase;
   (d) measuring the enzyme activity in either the liquid or the solid phase of step (c); and
   (e) relating the measured enzyme activity to the thyroxine-binding index in the serum.

2. Method as in claim 1 wherein the predetermined amount of thyroxine is in an amount of 100 to 500 ng per milliliter of serum.

3. Method as in claim 1 wherein the enzyme label is peroxidase.

4. Method as in claim 3 wherein the peroxidase-labeled thyroxine is in an amount of 1 to 10 mu/ml.

5. Method as in claim 1 wherein the anti-thyroxine is bound to a carrier.

6. Method as in claim 5 wherein the carrier is the inner wall of a test tube.

7. Test kit for determining the thyroxine-binding index in serum comprising the following separately contained components:
   (a) predetermined amount of thyroxine;
   (b) predetermined amount of enzyme-labeled thyroxine;
   (c) anti-thyroxine bound to a solid material;
   (d) buffer; and
   (e) reagent for determining the activity of said enzyme.

8. Test kit as in claim 7 consisting essentially of

| | |
|---|---|
| thyroxine | 100–400 ng/ml. |
| thyroxine-peroxidase | 5–100 mU/ml. |
| barbital buffer (pH 8.6) | 0.1–0.2 M |
| bovine serum albumin | 0.2% |
| antithyroxine (calculated without carrier) | 1–0.05/ng/ml. |
| hydrogen peroxidase | 0.5–5 mM/l. |
| 2,2'-azino-di-(3-ethylbenzthiazoline-6-sulphonate) | 5–50 mM/l. |
| phosphate-citrate buffer (pH. 5.0) | 0.1–0.2 M |

* * * * *